ic Patent [19] [11] 4,370,504
Ojima et al. [45] Jan. 25, 1983

[54] PROCESS FOR PRODUCING PERFLUOROCARBON GROUP-CONTAINING ALDEHYDES

[75] Inventors: Iwao Ojima; Takamasa Fuchikami, both of Sagamihara, Japan

[73] Assignee: Sagami Chemical Research Center, Japan

[21] Appl. No.: 240,361

[22] Filed: Mar. 4, 1981

[30] Foreign Application Priority Data

Mar. 7, 1980 [JP] Japan .................................. 55/28061

[51] Int. Cl.³ ............................................ C07C 45/50
[52] U.S. Cl. ..................................... 568/454; 568/909
[58] Field of Search ............... 568/451, 454, 888, 909, 568/882

[56] References Cited

FOREIGN PATENT DOCUMENTS 1414323 11/1976 United Kingdom .
1484117 8/1977 United Kingdom .

OTHER PUBLICATIONS

Falbe, "New Syntheses With Carbon Monoxide", (1980), Springer-Verlag, pp. 174-175.

Primary Examiner—Werren B. Lone
Attorney, Agent, or Firm—Wenderoth, Lind & Ponack

[57] ABSTRACT

A process for producing an aldehyde containing a perfluorocarbon group, which comprises hydroformylating an olefin containing a perfluorocarbon group represented by the general formula

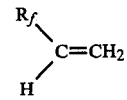

wherein $R_f$ represents a monovalent perfluorocarbon group, in the presence of a rhodium catalyst.

5 Claims, No Drawings

PROCESS FOR PRODUCING PERFLUOROCARBON GROUP-CONTAINING ALDEHYDES

This invention relates to a novel process for producing aldehydes containing a perfluorocarbon group. More specifically, it relates to a process for producing aldehydes containing a perfluorocarbon group by hydroformylation of olefins containing a perfluorocarbon group.

For production of perfluorocarbon group-containing aldehydes, a method has previously been proposed which comprises reacting perfluoroiodoalkanes with enamines in the presence of radical initiators (see British Patent Specification No. 1,484,117). According to this method, however, the yield of the intended aldehydes is low (about 25 to 30%).

British Patent Specification No. 1,414,323 discloses a method for producing an aldehyde of the formula $C_nF_{2n+1}CH_2CH_2CHO$ wherein n is a number of 1 to 20 which comprises reacting a fluoro-olefin of the formula $C_nF_{2n+1}CH=CH_2$ wherein n is as defined above with a gaseous mixture composed carbon monoxide and hydrogen which contains at least a stoichiometric amount of hydrogen and has a carbon monoxide partial pressure of at least 50 atmospheres in the presence of a cobalt catalyst at a temperature of about 120° C. to about 160° C. Although this method permits selective production of linear aldehydes, it cannot be used to produce branched aldehydes which are the intended products of the process of this invention.

The present inventors have made extensive investigations about conditions for producing fluorocarbon group-containing aldehydes in high yields by the hydroformylation of fluorocarbon group-containing olefins of the formula

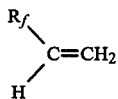

wherein $R_f$ represents a monovalent fluorocarbon group. These investigations have led to the surprising discovery that the performance of the aforesaid hydroformylation reaction in the presence of a rhodium catalyst yields preferentially a branched-chain aldehyde of the formula

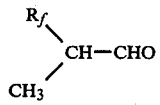

in exceedingly high yields, instead of a linear aldehyde of the formula

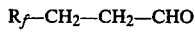

which is anticipated from the reaction described in the above-cited British Patent Specification No. 1,414,323.

According to this invention, there is provided a process for producing an aldehyde containing a perfluorocarbon group, which comprises hydroformylating an olefin containing a perfluorocarbon group represented by the general formula

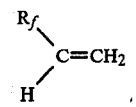

wherein $R_f$ represents a monovalent perfluorocarbon group, in the presence of a rhodium catalyst.

The "monovalent perfluorocarbon group", as used in the present application, denotes a group resulting from replacement of all of the hydrogen atoms attached to carbon atoms in a monovalent hydrocarbon group by fluorine atoms, and may include, for example, perfluoroalkyl groups, perfluoroaryl groups, perfluorocycloalkyl groups, and perfluoroaralkyl groups. These perfluorocarbon groups may generally contain up to 20 carbon atoms, preferably up to 8 carbon atoms. Suitable perfluorocarbon groups are linear or branched perfluoroalkyl groups having up to 20 carbon atoms, preferably up to 8 carbon atoms, such as trifluoromethyl, pentafluoroethyl, heptafluoropropyl, heptafluoro-iso-propyl, nonafluorobutyl, nonafluoro-iso-butyl, nonafluoro-sec-butyl, nonafluoro-tert-butyl, and perfluorooctyl; perfluoroaryl groups having 6 to 10 carbon atoms such as perfluorophenyl and perfluoronaphthyl, particularly perfluorophenyl; and perfluorocycloalkyl groups having 5 to 8 carbon atoms such as perfluorocyclohexyl.

Typical examples of the compound of formula (I) used as a starting material in the process of this invention include perfluoroalkylethylenes such as 3,3,3-trifluoropropene, 3,3,4,4,4-pentafluoro-1-butene, perfluoropropylethylene, perfluorooctylethylene, perfluoropentadecylethylene, perfluoroisopropylethylene, perfluoro-tert-butylethylene, perfluoroneopentylethylene and perfluorocyclohexylethylene; and perfluoroaryl- or perfluoroaralkylethylenes such as pentafluorostyrene, perfluorobenzylethylene and perfluoronaphthylethylene.

The compounds of formula (I) are known compounds, or may be produced easily by methods similar to those used in the production of these known compounds, for example by adding a perfluoroalkyl iodide to ethylene under radical conditions and then dehydroiodinating the adduct, or by radical-addition of a perchloroalkane to ethylene followed by treatment with hydrogen fluoride.

According to this invention, the perfluorocarbon group-containing olefin of formula (I) is hydroformylated in the presence of a rhodium catalyst. The rhodium catalyst used in the process of this invention includes, for example, a combination of monovalent rhodium and a tertiary phosphine or a phosphite, a combination of rhodium metal and a tertiary phosphine or a phosphite, a combination of trivalent rhodium and a tertiary phosphine or a phosphite, a combination of a rhodium carbonyl cluster compound and a tertiary phosphine or a phosphite, and products obtained by bonding the above catalyst systems to inorganic or organic carriers.

Examples of the rhodium catalyst are $Rh(PY_3)_3X$, $Rh(CO)(PY_3)_2X$, $HRh(CO)(PY_3)_3$, $Rh_6(CO)_{16}+mPY_3$, $Rh/C+mPY_3$, $RhCl_3+mPY_3$, $[RhCl(cyclooctadiene)]_2+mY_2P(CH_2)_2PY_2$, $[Rh(C_8H_{12})_2]^+Z^-+mPY_3$, $[Rh(norbornadiene)_2]^+Z^-+mY_2P(CH_2)_2PY_2$, and $[Rh(CO)_2Cl]_2+mPY_3$.

In the above exemplification, X represents a halogen atom; Y represents phenyl, substituted phenyl, phenoxy, substituted phenoxy, benzyl, substituted benzyl, alkyl, substituted alkyl, alkoxy, substituted alkoxy, or dialkylamino, preferably phenyl or phenoxy; Z represents ClO$_4$, BF$_4$, PF$_6$ or BPh$_4$, and m is a number of 1 to 50, preferably a number of 1 to 12. Examples of the substituents in the aforesaid substituted phenyl, phenoxy, benzyl, alkyl and alkoxy groups are p-tolyl, m-chlorophenyl, 3,4-dichlorophenyl, p-anisyl, p-dimethylaminophenyl, p-bromophenoxy, p-tolyloxy, m-anisylloxy, 3,4-dimethoxyphenoxy, p-dimethylaminobenzyl, p-chlorobenzyl, p-methylbenzyl, methyl, ethyl, propyl, butyl, hexyl, octyl, methoxy, ethoxy, propoxy, butoxy, hexyloxy, cyclohexyloxy and octyloxy.

Of the above rhodium catalysts, HRh(CO)(PPh$_3$)$_3$, Rh/C+2P(OPh)$_3$, Rh/C+2PPh$_3$, Rh$_6$(CO)$_{16}$+12PPh$_3$, [RhCl(C$_8$H$_{12}$)]$_2$+2Ph$_2$P(CH$_2$)$_4$PPh$_2$, Rh(PPh$_3$)$_3$Cl and Rh(CO)(PPh$_3$)$_2$Cl are especially preferred. Ph in these formulae represents phenyl.

The rhodium catalyst in the form of complex can generally be easily synthesized by methods known from the literature using rhodium chloride as a starting material [J. A. Osborn and G. Wilkinson, Inorg. Synth., 10, 67 (1967); D. Evans, J. A. Osborn and G. Wilkinson, Inorg. Synth., 11, 99 (1968); and D. Evans, G. Yagupsky, and G. Wilkinson, J. Chem. Soc., A., 1968, 2660]. Other catalyst systems can be easily prepared by simply mixing rhodium metal, rhodium salts, rhodium oxide, rhodium-carbonyl cluster compound, rhodium-carbonyl complex or rhodium-olefin complexes which are easily available commercially, with tertiary phosphines, phosphites, phosphonamides, etc.

The rhodium catalyst may be used in a catalytic amount, preferably in an amount of $10^{-2}$ to $10^{-6}$ mole, more preferably $10^{-3}$ to $10^{-5}$ mole, per mole of the perfluorocarbon group-containing olefin of general formula (I).

Hydroformylation of the compound of formula (I) in the presence of such a rhodium catalyst can be performed by reacting the perfluorocarbon group-containing olefin with carbon monoxide and hydrogen. Although varying with the type of the reactor used, etc., the amount each of carbon monoxide and hydrogen is generally 1 to 100 moles, preferably 1 to 5 moles, per mole of the olefin to be reacted.

The hydroformylation reaction may be carried out in the absence of a solvent. Generally, however, it is desirable to carry it out in an inert solvent.

Examples of inert solvents that can be advantageously used in the process of this invention include aromatic hydrocarbons such as benzene, toluene and xylene, hydrocarbons such as pentane, heptane, and octane, ethers such as tetrahydrofuran and dioxane, alcohols such as methanol and ethanol, carbonyl compounds such as acetone and methyl ethyl ketone, amines such as triethylamine and pyridine, amides such as dimethyl formamide, carboxylic acids such as acetic acid, and carboxylic acid esters such as ethyl acetate.

The hydroformylation can be performed usually by charging the perfluorocarbon group-containing olefin as a starting material into a pressure vessel such as an autoclave, and then feeding a gaseous mixture of carbon monoxide and hydrogen into the vessel.

The reaction pressure and temperature can be varied widely depending upon the type of the olefin used, etc. Generally, it is appropriate to use a pressure of generally from atmospheric pressure to 300 atmospheres, preferably from 30 to 100 atmospheres, and a temperature of generally from room temperature to 300° C., preferably 50° to 120° C.

The process of this invention described hereinabove yields preferentially a compound of the following formula

wherein R$_f$ is as defined above, in high yields.

This is highly contrastive to the fact that in the process set forth in the above-cited British Patent Specification No. 1,414,323, hydroformylation of a fluoro-olefin of the formula C$_n$F$_{2n}$CH=CH$_2$ in the presence of a cobalt catalyst yields a linear aldehyde of the formula C$_n$F$_{2n}$CHCH$_2$CHO with high selectivity.

The perfluorocarbon group-containing aldehydes of formula (II) provided by this invention can be used as intermediates for compounds which are useful as medicines, agricultural chemicals, dyes and functional polymeric materials such as photoresists. For example, oxidation of a compound of formula (II) in which R$_f$ is CF$_3$ (i.e., trifluoroisobutyraldehyde) obtained by the process of this invention gives trifluoroisobutyric acid, and its reduction gives trifluoroisobutyl alcohol. Trifluoroisobutyl alcohol is converted to isobutyl halides. Furthermore, a trifluorobutyroyl halide converted from the trifluoroisobutyraldehyde may be used as a reagent for introducing the trifluoroisobutyroyl group into various compounds. The Strecker reaction of trifluoriisobutyraldehyde gives trifluorovaline, and reaction of trifluoroisobutyraldehyde with an acylglycine gives trifluoroleucine which is useful as an antibacterial agent. A compound of formula (II) in which R$_f$ is C$_6$F$_5$ (ie., 2-pentafluorophenylpropionaldehyde) can be converted to pentafluorohydroatropic acid by oxidation.

The following Examples illustrate the present invention more specifically.

EXAMPLE 1

A 200 ml autoclave was charged with 28 mg (3.04×10$^{-2}$ millimoles) of chlorotris(triphenylphosphine)rhodium, 5.86 g (30.2 millimoles) of pentafluorostyrene and 20 ml of benzene as a solvent, and they were stirred at 90° C. for 20 hours while maintaining a carbon monoxide pressure of 40 atmospheres and a hydrogen pressure of 40 atmospheres. The absorption of hydrogen and carbon monoxide stopped, and the reaction came to completion. After releasing the pressure from the atuoclave, the reaction mixture was taken out from the autoclave. The solvent was distilled off, and the residue was distilled to give 6.65 g (yield 98%) of 2-pentafluorophenylpropanal having a boiling point of 40° C./1 mm Hg.

n$_D^{20}$: 1.4428

$^1$H NMR (CDCl$_3$): δ1.56 (d, J=7.4 Hz, 3H), 3.95 (m, 1H), 9.75 (t, J=2.2 Hz, 1H).

$^{19}$F NMR (CDCl$_3$: CF$_3$COOH): δ−63.28 (m, 2 F), −75.95 (t, J=20.9 Hz, 1 F), −82.91 (m, 2 F).

IR (neat): 2820, 2720 cm$^{-1}$(ν$_{C-H}$), 1740 cm$^{-1}$ (ν$_{C=O}$).

Elemental analysis: Found: C, 48.00; H, 2.21. Calculated: C, 48.23; H, 2.25.

EXAMPLE 2

A 200 ml autoclave was charged with 27.8 mg ($3.00 \times 10^{-2}$ millimoles) of chlorotris(triphenylphosphine)rhodium, 224 ml (10 millimoles) of 3,3,3-trifluoro-1-propene and 2 ml of toluene as a solvent, and they were stirred at 80° C. for 16 hours while maintaining a carbon monoxide pressure of 40 atmospheres and a hydrogen pressure of 40 atmospheres, thereby completing the reaction. Distillation of the reaction mixture gave 1.20 g (yield 95%) of 2-trifluoromethylpropanal having a boiling point of 66° C.

$^1$H NMR (CDCl$_3$): $\delta$1.31 (d, J=7.2 Hz, 3H), 3.09 (m, 1H), 9.79 (br.s, 1H).

$^{19}$F NMR (CDCl$_3$: CF$_3$COOH): $\delta$9.91 (d, J=9.6 Hz).

IR (neat): 2850, 2730 cm$^-$($\nu_{C-H}$), 1740 cm$^{-1}$ ($\nu_{C=O}$).

Simultaneously, 0.05 g of 4,4,4-trifluorobutanol was obtained.

EXAMPLES 3 TO 18

Example 1 was repeated except that 3,3,3-trifluoro-1-propene was used as the starting material and the reaction conditions shown in Table 1 were used. The results are shown in Table 1.

EXAMPLES 19 TO 24

Example 1 was repeated except that pentafluorostyrene was used as the starting material, and the conditions shown in Table 2 were used. The results are shown in Table 2.

TABLE 2

| Example No. | Reactor (ml.) | PFS[a] (mmol.) | Catalyst[c] | PFS/catalyst molar ratio | CO[b] (atm.) | H$_2$[b] (atm.) | Benzene (ml.) | Temp. (°C.) | Time (hr.) | Aldehyde Total (%) | (iso/n)[d] |
|---|---|---|---|---|---|---|---|---|---|---|---|
| 19 | 200 | 3 | A | 1000 | 40 | 40 | 3 | 90 | 2 | 98 | 98/2 |
| 20 | " | 100 | A | 1000 | 50 | 50 | 30 | 90 | 22 | 97 | 91/9 |
| 21 | " | " | A | 500 | 50 | 50 | 30 | 90 | 14 | 98 | 96/4 |
| 22 | " | " | A | 333 | 50 | 50 | 30 | 90 | 17 | 98 | 97/3 |
| 23 | " | " | A | 250 | 40 | 60 | 30 | 90 | 17 | 99 | 97/3 |
| 24 | " | " | B | 333 | 50 | 50 | 30 | 90 | 19 | 98 | 97/3 |

Note to Table 2
[a]PFS = pentafluorostyrene
[b]Initial pressure at 20° C.
[c]Catalyst A and B are the same as in Table 1.
[d]iso/n = the weight ratio of 2-pentafluorophenylpropanal (iso) to 3-pentafluorophenylpropanal (n) in the resulting aldehyde.

What we claim is:

1. A process for producing an aldehyde containing a perfluorocarbon group represented by the formula:

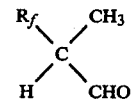

wherein $R_f$ represents a perfluoroalkyl group having up to 20 carbon atoms, a perfluoroaryl group having 6 to 10 carbon atoms, or a perfluorocycloalkyl group having 5 to 8 carbon atoms, which comprises reacting an olefin containing a perfluorocarbon group represented by the formula:

TABLE 1

| Example No. | Reactor (ml.) | TFP[a] (mmol.) | Catalyst[c] | TFP/catalyst molar ratio | CO[b] (atm.) | H$_2$[b] (atm.) | Toluene (ml.) | Temp. (°C.) | Time (hr.) | Aldehyde Total (%) | (iso/n)[d] |
|---|---|---|---|---|---|---|---|---|---|---|---|
| 3 | 200 | 120 | A | 1200 | 55 | 55 | 20 | 80 | 22 | 30 | 96/4 |
| 4 | " | " | B | " | " | " | " | " | " | 23 | 95/5 |
| 5 | " | " | C | " | " | " | " | " | 6 | 96 | 95/5 |
| 6 | " | " | D | " | " | " | " | " | 22 | 94 | 97/3 |
| 7 | " | " | E | " | " | " | " | " | " | 89 | 95/5 |
| 8 | " | " | F | " | " | " | " | " | " | 17 | 96/4 |
| 9 | " | " | G | " | " | " | " | " | 6 | 98 | 96/4 |
| 10 | " | " | H | " | " | " | " | " | 22 | 42 | 97/3 |
| 11 | " | " | C | " | 25 | 25 | " | " | 15 | 96 | 96/4 |
| 12 | " | 100 | A | 1000 | 40 | 40 | " | 90 | 20 | 66 | 94/6 |
| 13 | " | 50 | A | 500 | 50 | 50 | 10 | 100 | 44 | 97 | 95/5 |
| 14 | 200 | 100 | A | 1000 | 45 | 45 | 20 | 100 | 43 | 83 | 92/8 |
| 15 | 1000 | 1000 | A | 1000 | 70 | 70 | 200 | 100 | 21 | 94 | 93/7 |
| 16 | " | 1200 | A | 1200 | 80 | 80 | 200 | 100 | 20 | 94 | 91/8 |
| 17 | 200 | 120 | C | 1200 | 55 | 55 | 20 | 120 | 3 | 93 | 93/7 |
| 18 | 1000 | 1200 | C | 5000 | 40 | 40 | 200 | 90 | 6 | 95 | 96/4 |

Note to Table 1
[a]TFP = 3,3,3-trifluoro-1-propene [b]Initial pressure at 20° C.
[c]Catalyst A = RhCl(PPh$_3$)$_3$
Catalyst B = $RhCl(CO)(PPh_3)_2$
Catalyst C = $HRh(CO)(PPh_2)_3$
Catalyst D = $Rh_6(CO)_{16}$ + 12PPh$_3$
Catalyst E = $5\%Rh/C$ + 2PPh$_3$
Catalyst F = $RhCl_3 \cdot 3H_2O$ + 2PPh$_3$
Catallyst G = $5\%Rh/C$ + 2P(OPh)$_3$
Catalyst H = $[RhCl(1,5-cyclooctadiene)]_2$ + 1,4-bis(diphenylphosphinobutane)
[d]iso/n = the weight ratio of 2-trifluoromethylpropanal (iso) to 4,4,4-trifluorobutanal (n) in the resulting aldehyde.

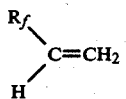

wherein $R_f$ is as defined above,
with carbon monoxide and hydrogen in the presence of a rhodium catalyst which is $Rh(PY_3)_3X$, $Rh(CO)(PY_3)_2X$, $HRh(CO)(PY_3)_3$, $Rh_6(CO)_{16}+mPY_3$, $Rh/C+mPY_3$, $RhCl_3+mPY_3$, $[RhCl(C_8H_{12})]_2+mYP(CH_2)_4PY_2$, $[Rh(C_8H_{12})_2]^+Z^-+mPY_3$, $[Rh(norbornadiene)_2]^+Z^-+mY_2P(CH_2)_2PY_2$, or $[Rh(CO)_2Cl]_2+mPY_3$, wherein X represents halogen, Y represents phenyl, substituted phenyl, phenoxy, substituted phenoxy, benzyl, substituted benzyl, alkyl, substituted alkyl, alkoxy, substituted alkoxy, or dialkylamino, Z represents $ClO_4$, $BF_4$, $PF_6$ or $BPh_4$, ph represents phenyl, and m is a number of 1 to 50.

2. The process of claim 1 wherein the rhodium catalyst is $HRh(CO)(PPh_3)_3$, $Rh/C+2P(OPh)_3$, $Rh/C+2PPh_3$, $Rh_6(CO)_{16}+2PPh_3$, $[RhCl(cyclooctadiene)]_2+2Ph_2P(CH_2)_4-PPh_2$, $Rh(PPh_3)_3Cl$ and $Rh(CO)(PPh_3)_2Cl$.

3. The process of claim 1 wherein the amount of the rhodium compound is $10^{-2}$ to $10^{-6}$ mole per mole of the perfluorocarbon group-containing olefin.

4. The process of claim 1 wherein the hydroformylation is carried out at a temperature from room temperature to 300° C.

5. The process of claim 1 wherein the hydroformylation is carried out at a pressure from atmospheric pressure to 300 atmospheres.

* * * * *